United States Patent [19]

Tanaka et al.

[11] Patent Number: 4,950,780
[45] Date of Patent: Aug. 21, 1990

[54] N-OCTADECYL-3-(3,5-DI-T-BUTYL-4-HYDROXYPHENYL)PROPIONATE WITH A NOVEL CRYSTALLINE FORM

[75] Inventors: Masaya Tanaka; Masayoshi Gohbayashi; Kunihide Oka, all of Nakatsu, Japan

[73] Assignee: Yoshitomi Pharmaceutical Industries, Ltd., Osaka, Japan

[21] Appl. No.: 402,812

[22] Filed: Sep. 5, 1989

[30] Foreign Application Priority Data

Sep. 5, 1988 [JP] Japan .................... 53-223024

[51] Int. Cl.$^5$ ............................................. C07C 69/76
[52] U.S. Cl. .................................................... 560/75
[58] Field of Search .......................................... 560/75

[56] References Cited

U.S. PATENT DOCUMENTS 3,285,855 11/1966 Dexter et al. .................. 252/57
3,330,859 7/1967 Dexter et al. .................. 260/473
4,085,132 4/1978 Park et al. ...................... 560/75
4,377,666 3/1983 Farrar .............................. 560/75

FOREIGN PATENT DOCUMENTS

| 875150 | 7/1979 | Belgium . |
| EP33395 | 8/1981 | European Pat. Off. . |
| EP68851 | 1/1983 | European Pat. Off. . |
| 333464 | 9/1989 | European Pat. Off. . |
| 3843082 | 7/1989 | Fed. Rep. of Germany . |

OTHER PUBLICATIONS

Koch, J. et al., Fette, Selfen, Austrichm, 78(9) 371–7, 1976.

Primary Examiner—Paul J. Killos
Attorney, Agent, or Firm—Wenderoth, Lind & Ponack

[57] ABSTRACT

Novel crystalline form of n-octadecyl-3-(3,5-di-t-butyl-4-hydroxyphenyl)propionate with improved transportability, measurability and workability is disclosed.

2 Claims, 3 Drawing Sheets

N-OCTADECYL-3-(3,5-DI-T-BUTYL-4-HYDROXY-PHENYL)PROPIONATE WITH A NOVEL CRYSTALLINE FORM

BACKGROUND OF THE INVENTION

This invention relates to a novel crystalline structure of n-octadecyl-3-(3,5-di-t-butyl-4-hydroxyphenyl)propionate (hereinafter referred to as compound (I)) as an industrially useful antioxidant.

The aforesaid compound (I) already available on the market is white fine powders with low bulk density, which is easily diffused into air during various handlings and not satisfactory in transportability, workability and measurability thereof.

The present inventors have found that the aforesaid problems can be solved by the flake-like compound (I) with good quality, which was obtained by melt granulation and melt solidification.

Based on further research works, the inventors have found that the selected conditions of the melt solidification gave the compound (I) a novel crystalline structure quite different from the crystalline structures of prior commercial products. These findings resulted in the accomplishment of this invention.

SUMMARY OF THE INVENTION

This invention relates to (1) n-octadecyl-3-(3,5-di-t-butyl-4-hydroxyphenyl)propionate with a novel crystalline structure (hereinafter sometimes referred to as α-crystal) showing a sharp X-ray diffraction peak at the diffraction angle $2\theta = 19.10$ when measured with X-ray of Cu-Kα wavelength and (2) n-octadecyl-3-(3,5-di-t-butyl-4-hydroxyphenyl)propionate with a novel crystalline structure (hereinafter sometimes referred to as β-crystal) showing a sharp X-ray diffraction peak at the diffraction angle $2\theta$ 32 19.48 when measured with X-ray of Cu-Kα wavelength.

BRIEF EXPLANATION OF THE DRAWINGS

FIG. 1 and FIG. 2 respectively show X-ray diffraction patterns of α- and β-crystals of the compound (I), while

DETAILED DESCRIPTION

According to this invention, the novel α-crystal of the compound (I) is obtained by melting the compound (I) at 60–80° C. and subsequent cooling thereof to 30–50° C., while the β-crystal is obtained by melting the compound (I) at 55–75° C. and subsequent cooling thereof to 20–30° C. Stirring operation may be applied if necessary.

The compound (I) used in this invention is prepared normally by a known ester-exchange method between octadecyl alcohol and 3-(3,5-di-t-butyl-4-hydroxyphenyl)propionic acid alkyl ester (preferably methyl ester and ethyl ester).

Figure 1:
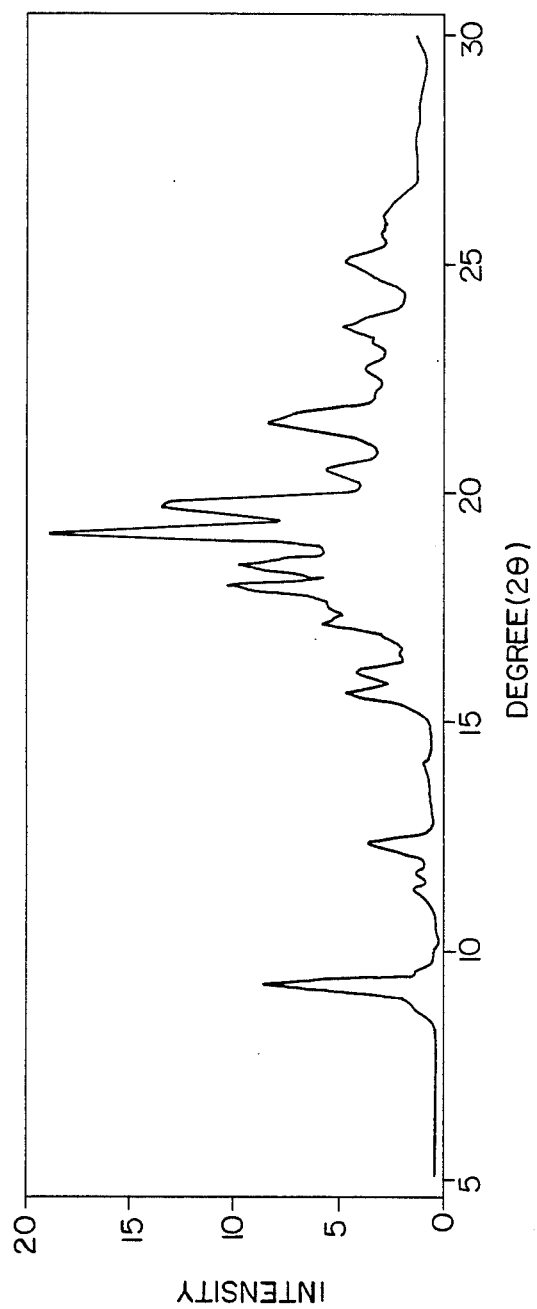

The α-crystal obtained according to this invention has a diffraction pattern measured with X-ray (Cu-Kα), namely, X-ray diffraction intensity to the diffraction angle $2\theta$ as shown in Table 1 and an X-ray diffraction spectrum as shown in FIG. 1. Specifically, the sharp X-ray diffraction peak at the diffraction angle $2\theta = 19.10$ enables provision of n-octadecyl-3-(3,5-di-t-butyl-4-hydroxyphenyl)propionate with a novel crystalline structure distinguishable from conventional commercial products (powders, hereinafter sometimes referred to as γ-crystals). It is a characteristic of this invention that the melting point thereof is 45–47° C., slightly lower than that of the conventional products.

TABLE 1

| No. | Diffraction angle 2θ (°) | d (A) | Relative intensity I/I₁ (%) |
|---|---|---|---|
| 1 | 25.991 | 3.4252 | 11 |
| 2 | 25.557 | 3.4824 | 12 |
| 3 | 25.015 | 3.5566 | 25 |
| 4 | 23.551 | 3.7743 | 24 |
| 5 | 22.575 | 3.9353 | 15 |
| 6 | 21.653 | 4.1007 | 48 |
| 7 | 20.406 | 4.3485 | 21 |
| 8 | 19.701 | 4.5025 | 73 |
| 9 | 19.104 | 4.6417 | 100 |
| 10 | 18.399 | 4.8179 | 50 |
| 11 | 17.911 | 4.9481 | 52 |
| 12 | 17.097 | 5.1816 | 26 |
| 13 | 16.013 | 5.5301 | 18 |
| 14 | 15.579 | 5.6831 | 22 |
| 15 | 12.217 | 7.2386 | 18 |
| 16 | 9.126 | 9.6824 | 48 |

Figure 2:
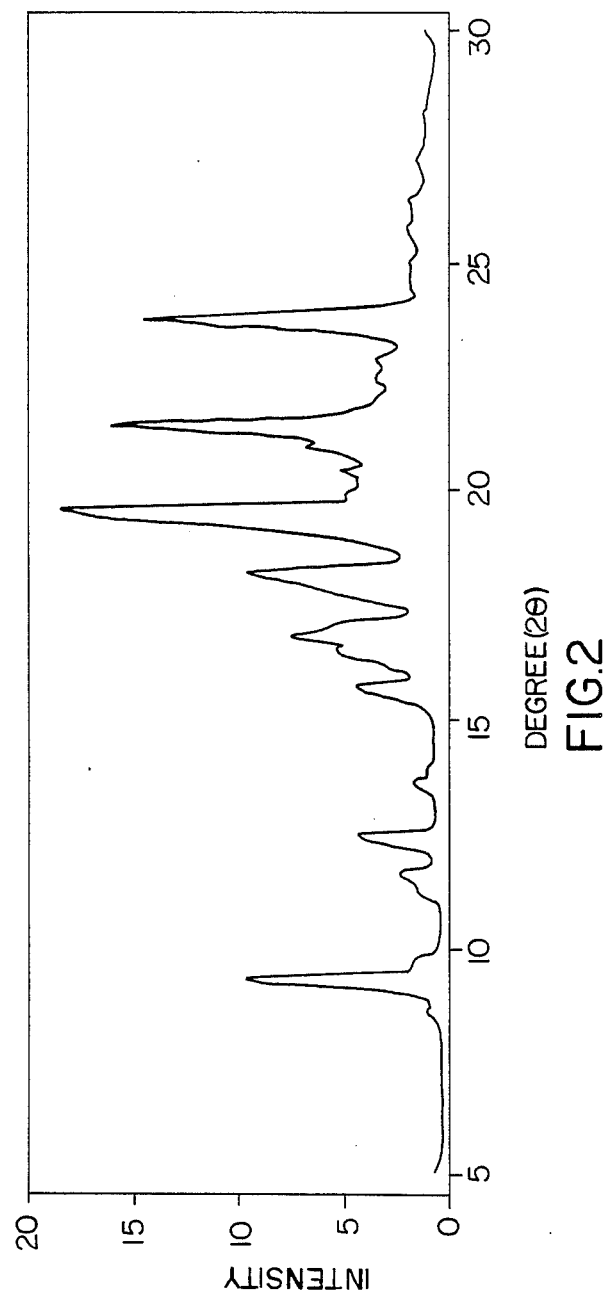

On the other hand, the β-crystal compound (I) has a diffraction pattern measured with X-ray (Cu-Kα), namely, X-ray diffraction intensity to the diffraction angle $2\theta$ as shown in Table 2 and an X-ray diffraction spectrum as shown in FIG. 2. The β-crystal compound (I) is characterized by a sharp diffraction peak at the diffraction angle $2\theta = 19.48$ and other 2 sharp peaks at the diffraction angle $2\theta = 15$–20, which the aforesaid α-crystal does not show. Moreover, the melting point of the β-crystal is 51–53° C., somewhat higher than that of the α-crystal.

TABLE 2

| No. | Diffraction angle 2θ (°) | d (A) | Relative intensity I/I₁ (%) |
|---|---|---|---|
| 1 | 23.714 | 3.7488 | 90 |
| 2 | 22.737 | 3.9075 | 12 |
| 3 | 22.412 | 3.9635 | 15 |
| 4 | 21.436 | 4.1417 | 73 |
| 5 | 20.406 | 4.3485 | 19 |
| 6 | 19.972 | 4.4419 | 15 |
| 7 | 19.484 | 4.5521 | 100 |
| 8 | 18.182 | 4.8749 | 44 |
| 9 | 16.826 | 5.2645 | 32 |
| 10 | 15.633 | 5.6635 | 19 |
| 11 | 12.325 | 7.1751 | 17 |
| 12 | 11.566 | 7.6443 | 9 |
| 13 | 9.234 | 9.5689 | 41 |

Figure 3:
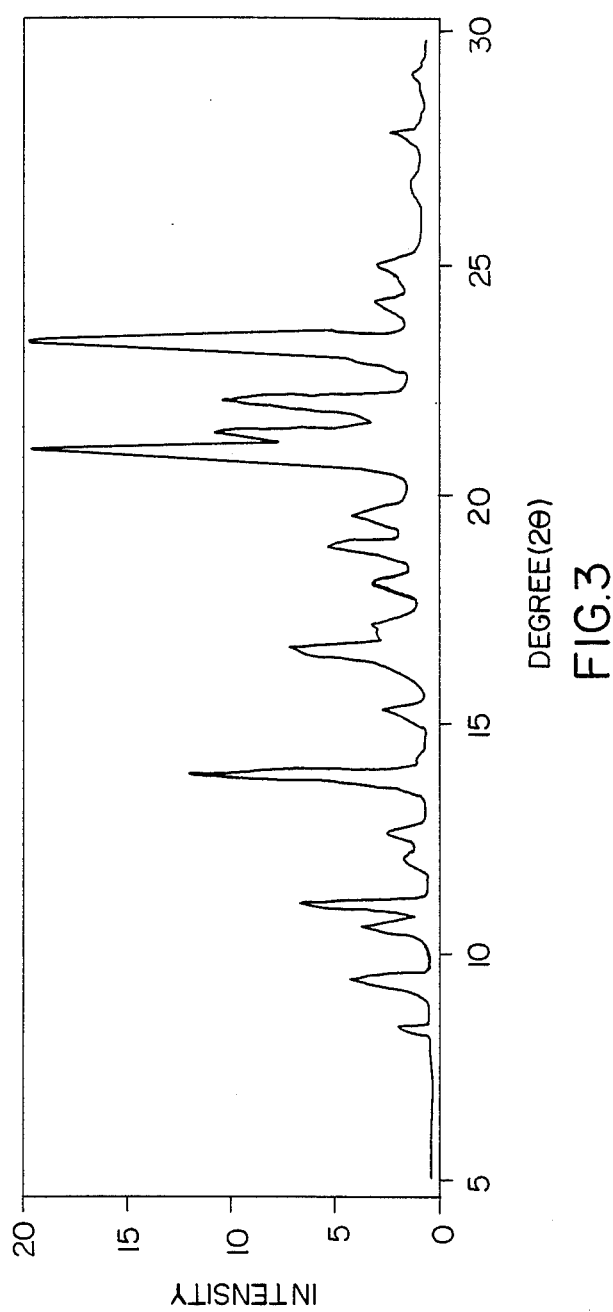
FIG. 3 shows an X-ray diffraction pattern of the conventional compound (I) (γ-crystal).

Meanwhile, conventional pulverous γcrystals of the compound (I) have a diffraction pattern measured with X-ray (Cu-Kα), namely, X-ray diffraction intensity to the diffraction angle $2\theta$ as shown in Table 3 and X-ray diffraction spectrum as shown in FIG. 3. Specifically, the γ-crystals show a sharp diffraction peak at the diffraction angle $2\theta = 23.225$ and the melting point thereof is 51–55° C.

TABLE 3

| No. | Diffraction angle 2θ (°) | d (A) | Relative intensity I/I₁ (%) |
|---|---|---|---|
| 1 | 27.889 | 3.1963 | 6 |
| 2 | 24.961 | 3.5642 | 10 |
| 3 | 24.093 | 3.6906 | 9 |
| 4 | 23.225 | 3.8265 | 100 |
| 5 | 21.924 | 4.0506 | 43 |
| 6 | 21.273 | 4.1730 | 33 |
| 7 | 20.894 | 4.2480 | 66 |
| 8 | 19.484 | 4.5521 | 10 |
| 9 | 18.833 | 4.7079 | 14 |

TABLE 3-continued

| No. | Diffraction angle 2θ (°) | d (A) | Relative intensity I/I₁ (%) |
|---|---|---|---|
| 10 | 18.019 | 4.9186 | 7 |
| 11 | 17.043 | 5.1980 | 6 |
| 12 | 16.555 | 5.3501 | 21 |
| 13 | 13.789 | 6.4164 | 33 |
| 14 | 10.969 | 8.0587 | 17 |
| 15 | 10.427 | 8.4765 | 10 |
| 16 | 9.288 | 9.5131 | 12 |

The α- and β-crystal according to this invention are characterized by higher bulk density and absence of dispersion thereof into air and useful as an antioxidant with improved transportability, measurability and workability. Hereinafter this invention will be described in detail by examples.

EXAMPLE 1

Pulverous n-octadecyl-3-(3,5-di-t-butyl-4-hydroxyphenyl)propionate (γ-crystal) was flaked at the melted liquid temperature of 70° C., the cooling drum temperature of 30° C. and rotating speed of 1.25 rpm by a rotary drum type flaker (0.5 m²). The powder characteristics of flakes obtained are represented by bulk specific gravity of 0.38, orifice diameter of 6.3 mm and pause angle of 39° C. This flake-like compound (I) was identified as the α-crystal as shown in Table 1 through X-ray diffraction analysis. The melting point measured by a measuring device with microscope for trace samples was 47.7–51.9° C. Liquid phase chromatography identified the purity of 99.02%. Moreover, the α-crystal (10 g) was dissolved in toluene to prepare exactly 100 ml solution, which was subjected to transmission measurement and showed the transmissibility of 99.3% to visible light of 425 nm in a cell of 1 cm width.

EXAMPLE 2

The pulverous compound (I) as used in the aforesaid Example 1 was flaked at the melted liquid temperature of 72° C., the cooling drum temperature of 25° C. and the rotating speed of 1.3 rpm in the same device used in Example 1. The α-crystal was obtained.

EXAMPLE 3

The same pulverous compound (I) used in Example 1 was flaked at the melted liquid temperature of 71° C., the cooling drum temperature of 26° C. and the rotating speed of 1.3 rpm in the same device used in Example 1. The β-crystal of the compound (I) was obtained.

EXAMPLE 4

The same pulverous compound (I) used in Example 1 was flaked at the melted liquid temperature of 58° C., the cooling drum temperature of 25° C. and the rotating speed of 1.3 rpm in the same device used in Example 1. The β-crystal was obtained.

The crystals obtained in the aforesaid Examples are compared with commercial pulverous products in Table 4.

TABLE 4

| | | Examples | | | | Commercial products | |
|---|---|---|---|---|---|---|---|
| | | 1 | 2 | 3 | 4 | A | B |
| Melted Liquid temperature (°C.) | | 70 | 72 | 71 | 58 | — | — |
| Drum cooling temperature (°C.) | | 30 | 25 | 26 | 25 | — | — |
| Drum rotating speed (rpm) | | 1.25 | 1.3 | 1.3 | 1.3 | — | — |
| Crystalline structure | | α-crystal | α-crystal | β-crystal | β-crystal | γ-crystal | γ-crystal |
| Properties | Appearance | Flaky | Flaky | Flaky | Flaky | Pulverous | Pulverous |
| | Melting point (°C.) | 47.7–51.9 | 47.7–51.9 | 51.3–52.7 | 51.3–52.7 | 51.0–53.0 | 51.2–52.7 |
| | Purity (%) | 99.02 | 99.01 | 99.02 | 99.02 | 99.02 | 99.02 |
| | Transmissibility (%) | 99.3 | 99.2 | 99.5 | 99.5 | 99.5 | 99.3 |
| | Bulk density | 0.38 | 0.38 | 0.38 | 0.36 | — | — |
| | Orifice diameter (mm) | 6.3 | 10 | 10 | 12.5 | not less than 25 | not less than 25 |
| | Pause angle (°) | 38 | 39 | 38 | 38 | 57 | 57 |

While this invention has been described by the foregoing specification including working examples, the embodiment described herein can be changed and modified in various manners within the scope and the spirit of this invention.

What is claimed is:

1. n-Octadecyl-3-(3,5-di-t-butyl-4-hydroxyphenyl)-propionate with a novel crystalline structure showing a sharp X-ray diffraction peak at the diffraction angle $2\theta = 19.10$ when measured with X-ray of Cu-Kα wavelength.

2. n-Octadecyl-3-(3,5-di-t-butyl-4-hydroxyphenyl)-propionate with a novel crystalline structure showing a sharp X-ray diffraction peak at the diffraction angle $2\theta = 19.48$ when measured with X-ray of Cu-Kα wavelength.

* * * * *